US00PP18699P2

(12) United States Plant Patent
Austin

(10) Patent No.: US PP18,699 P2
(45) Date of Patent: Apr. 1, 2008

(54) SHRUB ROSE PLANT NAMED 'AUSROVER'

(50) Latin Name: *Rosa hybrida*
Varietal Denomination: AUSrover

(75) Inventor: David C. H. Austin, Wolverhampton (GB)

(73) Assignee: David Austin Roses Limited, Albrighton, Wolverhampton (GB)

( * ) Notice: Subject to any disclaimer, the term of this patent is extended or adjusted under 35 U.S.C. 154(b) by 0 days.

(21) Appl. No.: 11/635,306

(22) Filed: Dec. 6, 2006

(51) Int. Cl.
*A01H 5/00* (2006.01)

(52) U.S. Cl. ..... Plt./105

(58) Field of Classification Search ..... Plt./105
See application file for complete search history.

*Primary Examiner*—Kent Bell
*Assistant Examiner*—S. B. McCormick-Ewoldt
(74) *Attorney, Agent, or Firm*—Kauth, Pomeroy, Peck & Bailey LLP

(57) ABSTRACT

A new and distinct variety of shrub rose plant substantially as herein shown and described, characterized particularly by a tall, upright and almost thornless shrub; having quartered, rosette shaped blooms of a rich apricot color; and a strong complex fragrance of tea, myrrh and fruit.

1 Drawing Sheet

Genus and species: *Rosa hybrida.*
Variety denomination: 'AUSrover'.

ORIGIN OF THE INVENTION

The present invention relates to a new and distinct variety of a shrub rose plant named 'AUSrover' which was originated by me by crossing an unnamed, unpatented seedling with an unnamed, unpatented seedling.

BACKGROUND OF THE INVENTION

The primary objective of this breeding was to produce a repeat flowering, very healthy rose plant with fragrant apricot blooms on a tall shrub.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Quartered, rosette shaped blooms of a rich apricot color.
2. A tall, upright and almost thornless shrub.
3. A strong, complex fragrance of tea, myrrh and fruit.

Asexual reproduction of this new variety by budding, as performed at Albrighton, England, shows that the foregoing and all other characteristics and distinctions come true to form and are established and transmitted through succeeding propagations.

COMPARISON WITH PARENTS

The seed parent has stiffer, more upright growth than 'AUSrover' which has a more rounded, bushy growth, and has more deeply cupped blooms than 'AUSrover'. The pollen parent has shorter growth than 'AUSrover' with yellow cupped blooms compared to the apricot quartered, rosette-shaped blooms of 'AUSrover'.

COMPARISON WITH SIMILAR VARIETY

'AUSkeppy' (not patented) has fewer petals per bloom than 'AUSrover' and the blooms are deeper apricot in color. 'AUSrover' has fewer prickles than 'AUSkeppy' and its petals have a more rounded apex.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling (Unpatented).

FLOWER

Observations made from plants commencing at one year of age grown in a garden environment at Albrighton, England.

Blooming habit: Recurrent. The number of blooms per plant during the growing season is profuse — there are too many to count.

Bud:
*Size.*—About 2.5 cm long and 1.5 cm in diameter when the petals start to unfurl.
*Form.*—The bud form is pointed ovoid.
*Color.*—When sepals first divide, bud color is Yellow-Orange Group 22A and Orange-Red Group N34A close to sepals and base. When half blown, the upper sides of the petals are Yellow-Orange Group 23C top half of petal, Yellow Group 12B basal half, and the lower sides of the petals are Yellow-Orange Group 23C top half of petal, and Yellow Group 12B basal half.

*Sepals.*—Color: Upper surface: Yellow-Green Group 144B. Lower surface: Yellow-Green Group N144C. Length: 2.7 cm. Width: 1.0 cm. Shape: Subulate. Surface texture: Upper surface: Pubescent. Lower surface: Rough, some glands. There are three lightly appendaged sepals. There are two unappendaged sepals with canescent edges.

*Receptacle.*—Color: Yellow-Green Group 144A. Shape: Campanulate. Size: Medium, about 0.9 cm long×0.9 cm wide. Surface: Smooth.

*Peduncle.*—Length: Medium, averaging about 4–5 cm. Surface: Very glandular. Color: Yellow-Green Group 144A. Strength: Normal.

Bloom:

*Size.*—Large. Average open diameter is about 9.3 cm.

*Borne.*—In irregular compound corymb clusters of four to five blooms.

*Form.*—When first open: Cupped. Permanence: Outer petals curl back.

*Petalage.*—Number of petals under normal conditions: 100.

*Color.*—The upper sides of the outer and middle petals are Yellow-Orange Group 14D top half, Yellow Group 12B basal half. The upper sides of the inner petals are Yellow-Orange Group 22D top half and Yellow Group 12A basal half. The reverse sides of the outer and middle petals are Yellow-Orange Group 14D top half, Yellow Group 12B basal half. The inner petals are Yellow-Orange Group 20B top half and Yellow Group 12A basal half.

*Variegations.*—None.

*Discoloration.*—The general tonality at the end of the first day is Yellow-Orange Group 14D. At the end of the third day: Yellow Group 13D and 12B.

*Fragrance.*—Strong tea, myrrh and fruit.

Petals:

*Texture.*—Smooth.

*Size.*—Width: 1.9 cm. Length: 3.6 cm.

*Surface.*—Smooth.

*Shape.*—Obovate. Margin: Notched. Apex Shape: Some obcordate, some obtuse. Base Shape: Cuneate. Form: Incurved, tips recurved and all very outer petals recurved.

*Arrangement.*—Quartered.

*Petaloids.*—Number: None.

*Persistence.*—Petals drop off cleanly before drying.

*Lastingness.*—On the plant: Fair (about 4 days). As a cut flower: Fair (about 4 days).

Reproductive parts:

*Stamens.*—Number: 10–15. Length: 5 mm. Anthers: Length: 2 mm. Color: Yellow Group 13A. Arrangement: Regular around styles. Filaments: Color: Yellow Group 8B. Length: 3 mm. Pollen: Color: Yellow Group 13A.

*Pistils.*—Number: 65–70. Length: 11 mm. Styles: Color: Yellow Group 8C. Length: 10 mm. Stigmas: Color: Yellow Group 11A. Length: 1 mm.

*Hips.*—None observed.

PLANT

*Form.*—Shrub.

*Growth.*—Medium vigor, bushy.

*Age at maturity.*—Two years.

*Mature plant.*—Height: 1.2 mm. Width: 1.0 m.

*Rootstock.*—'Dr. Huey' in the USA *Rosa dumetorum* 'Laxa' for the observed plants in the U.K.

Foliage: Number of leaflets on normal mid-stem leaves: 5–7 (including terminal leaflet).

*Size.*—Medium. About 15.9 cm long×11.5 cm wide.

*Quantity.*—Normal. Average number leaves per flowering stem: 7.

*Color.*—New foliage: Upper side: Yellow-Green Group 152A with Greyed-Purple Group 185A concentrated around margin. Lower side: Greyed-Purple Group 185A. Old foliage: Upper side: Green Group 139A. Lower side: Yellow-Green Group 147B.

Leaflets:

*Size.*—About 6 cm long×4.8 cm wide.

*Shape.*—Broadly oval.

*Base shape.*—Rounded.

*Apex shape.*—Acuminate.

*Texture.*—Smooth, dull/matt.

*Edge.*—Serrated.

*Serrations.*—Mainly large single.

*Petiole.*—Color: Yellow-Green Group 144A. Length: 4.5–5.5 cm. Width: 2 mm. Surface texture: Smooth, with prickles on underside.

*Petiole rachis.*—Color: Yellow-Green Group N144D. Underside: With prickles.

*Stipules.*—Length: 2 cm, glandular. Color: Green Group 143B.

*Auricle shape.*—Subulate. Length: 1 cm. Width: 2 mm at the base, tapering to a point. Color: Green Group 143B.

*Disease resistance.*—Resistant to powdery and downy mildew, blackspot and rust in normal growing conditions.

*Pest resistance.*—Not tested.

*Vein color.*—Yellow-Green Group N144D.

*Venation pattern.*—Reticulate.

Wood:

*New wood.*—Color: Yellow-Green Group 146C. Bark: Smooth.

*Old wood.*—Color: Yellow-Green Group 146A. Bark: Smooth.

Stems:

*Strength.*—Normal.

*Mature stem.*—Length: 40 cm. Diameter: 5 mm.

*Internode distance.*—7–8 cm. The above measurements are all variable, depending on growing conditions in a season.

Prickles:

*Quantity.*—On main canes from base: Few, 2 per 10 cm stem length. On laterals from main cases: Few, 2 per 30 cm per stem length.

*Form.*—Concave curved inward.

*Length.*—6 mm.

*Color when young.*—Red Group 47A.

*Color when mature.*—Greyed-Yellow Group 161B.

Small prickles:

*Quantity.*—On main stalks: None. On laterals: None.

Winter hardiness: Not tested.

I claim:

1. A new and distinct variety of shrub rose plant substantially as herein shown and described, characterized particularly by a tall, upright and almost thornless shrub; having quartered, rosetted shaped blooms of a rich apricot color; and a strong complex fragrance of tea, myrrh and fruit.

* * * * *

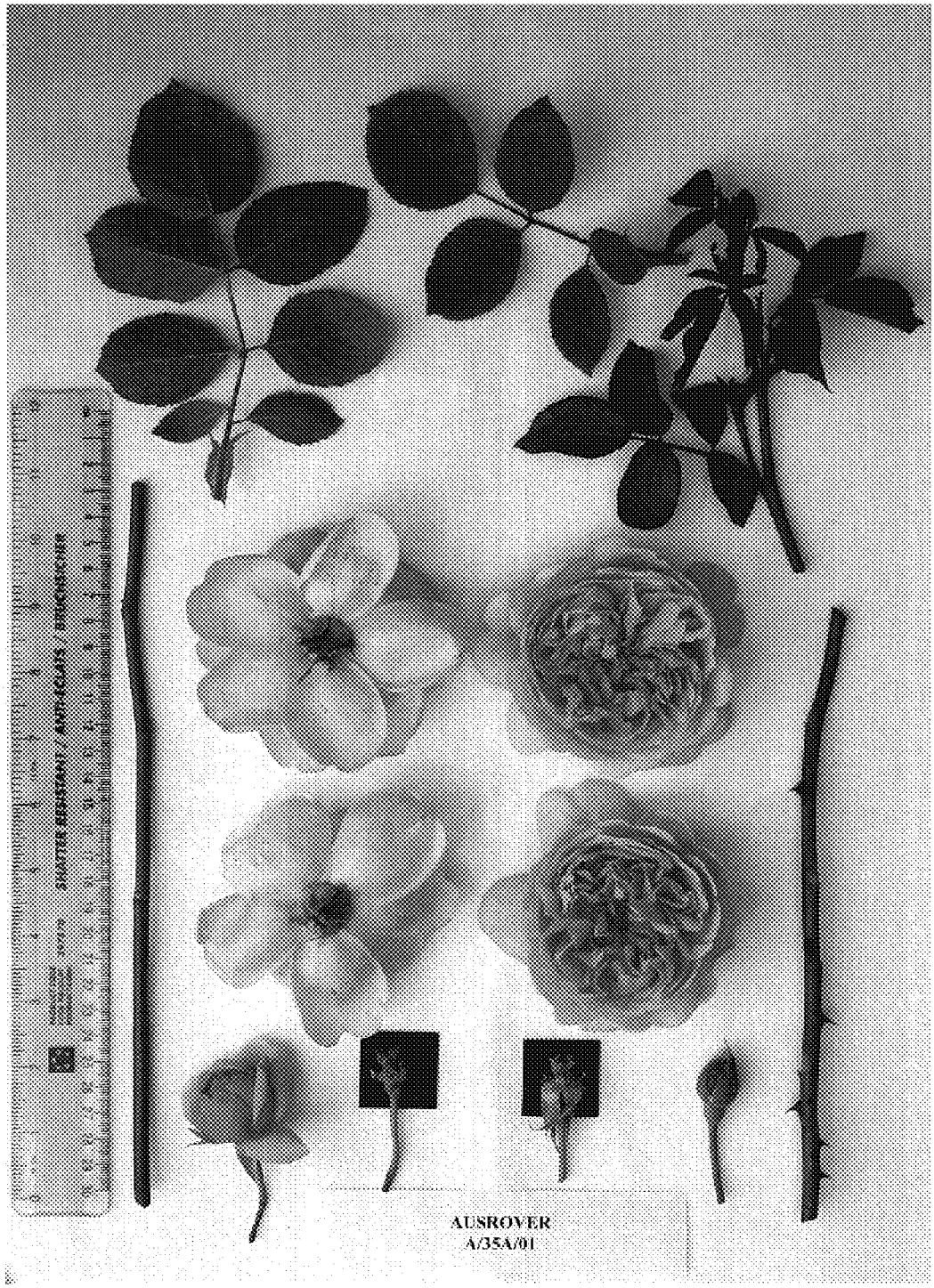
SHATTER RESISTANT / ANTI-GLARE / DIMENSIONS
AUSROVER
A/35A/01